United States Patent

Trinh et al.

[11] 4,076,807
[45] Feb. 28, 1978

[54] PHOSPHITE-BASED FUNGICIDE COMPOSITIONS

[75] Inventors: Stephane Trinh, Champagne-au-Mont d'Or; Alain Moraly, Lyon; Jean-Michel Gaulliard, Orlienas, all of France

[73] Assignee: Philagro S.A., France

[21] Appl. No.: 620,379

[22] Filed: Oct. 7, 1975

[30] Foreign Application Priority Data

Oct. 8, 1974 France .................. 74 34529

[51] Int. Cl.² ............................................. A01N 9/36
[52] U.S. Cl. ............................. 424/209; 260/937
[58] Field of Search ............................... 424/209

[56] References Cited

PUBLICATIONS

Zwierzak, "Canadian Jour. of Chem.," vol. 45, No. 21, (1967), pp. 2501–2504.
Oswald, "Canadian Jour. of Chem.," vol. 37, No. 9, (1959), pp. 1498–1501.

*Primary Examiner*—V. D. Turner
*Attorney, Agent, or Firm*—Robert E. Burns; Emmanuel J. Lobato; Bruce L. Adams

[57] ABSTRACT

Fungicidal compositions are disclosed which contain as active material at least one compound of the formula

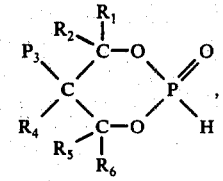

and

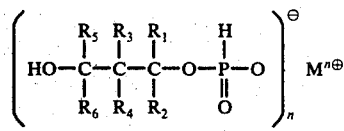

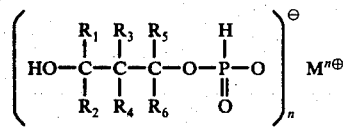

in which each of $R_1$, $R_2$, $R_3$, $R_4$, $R_5$ and $R_6$ may be identical or different and represent hydrogen, alkyl or halogenated alkyl containing 1 to 5, and preferably 1 to 3 carbon atoms, M represents hydrogen, a metal, an ammonium radical, an ammonium radical or an alkanolammonium radical, and $n$ is a whole number equal to the valency of M.

4 Claims, No Drawings

PHOSPHITE-BASED FUNGICIDE COMPOSITIONS

The present invention is concerned with phosphite-based fungicide compositions.

In particular, it concerns composition which may be used in the control of parasitic fungi of plants and which contain as active material at least one compound of at least one of the formulae:

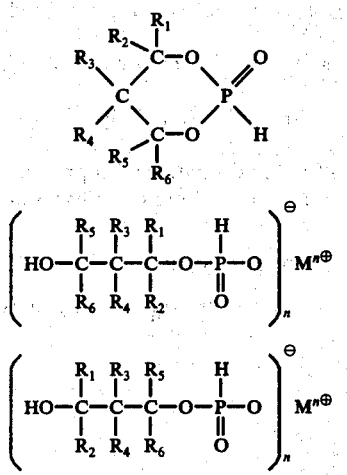

in which $R_1$, $R_2$, $R_3$, $R_4$, $R_5$, $R_6$, identical or different, represent an atom of hydrogen or an alkyl radical, possibly halogenated; containing 1 to 5, and preferably 1 to 3, carbon atoms, M represents a hydrogen or metal atom, or an ammonium, alkyl- or alkanol-ammonium radical, and $n$ is a whole number equal to the valency of M.

Among the usable metals may be cited the alkali and alkali-earth metals, such as sodium, potassium, barium, calcium, magnesium, or heavier metals, such as iron, copper, zinc, manganese, nickel, cobalt, aluminium, and mercury.

The invention also concerns fungicide compositions which may be used in the control of mildew affecting vines (*Plasmopara viticola*), tobacco (*Peronospora tabacci*), and hops (*Pseudoporonospora humili*), containing as active material a mixture of two or several compounds fitting the formulae (I), ($II_A$), and ($II_B$) mentioned above.

These compounds are themselves known as intermediates in the formation of other phosphorus compounds. A certain number of syntheses exist in the literature for their preparation.

The cyclic derivatives fitting the formula (I) can for example be prepared by hydrolysis, in an anhydrous solvent, particularly benzene or dioxane, of a 2-chloro-1,3,2-dioxaphosphorinane, according to the reaction:

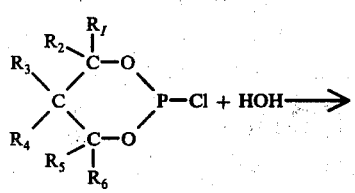

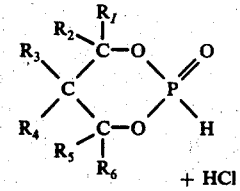

The resulting hydrochloric acid can either be fixed by working in an alkaline medium, or be driven off in gaseous form. In the latter case, the liberation is favored by maintaining a temperature close to ambient.

Following this procedure, 2-hydroxy-1,3,2-dioxaphosphorinane has been obtained.

In a 500 cc flask is placed 0.2 mole (3.6 g) of water and 250 cc of anhydrous benzene. Then, fairly rapidly, 0.2 mole (28.1 g) of 2-chloro-1,3,2-dioxaphosphorinane dissolved in 100 cc of anhydrous benzene is added. The temperature of the medium rises from 25° C to 40° C. The reaction is left to proceed with shaking for 10 minutes. The solvent is driven off and the resulting product rectified.

B.P. —90°—100° C/0.03 mm Bg
$n_D^{20}$ — 1.458
Yield — 90.2%

| Analysis | Percentage analysis for $C_3H_7O_3P$ | | |
|---|---|---|---|
| | C% | H% | P% |
| Calculated | 29.51 | 5.74 | 25.41 |
| Found | 29.20 | 6.08 | 25.17 |

Following this method, 2-hydroxy-4-methyl-1,3,2-dioxaphosphorinane has also been prepared:
M.P. — 53.4° C

| Analysis | Percentage analysis for $C_4H_9O_3P$ | | |
|---|---|---|---|
| | C% | H% | P% |
| Calculated | 35.3 | 6.62 | 22.8 |
| Found | 35.29 | 6.46 | 22.64 | as well as -
2-hydroxy-5,5-dimethyl-1,3,2-dioxaphosphorinane
B.P. — 100°-104° C/0.1 mm Hg
$n_D^{20}$ — 1.454
and
2-hydroxy-4,6-dimethyl-1,3,2-dioxaphosphorinane
Yield — 90%
B.P. — 100°-115° C/0.02 mm Hg
$n_D^{20}$ — 1.448

| Analysis | Percentage analysis for $C_5H_{11}O_3P$ | | |
|---|---|---|---|
| | C% | H% | P% |
| Calculated | 40.00 | 7.33 | 20.67 |
| Found | 40.26 | 7.19 | 20.63 | and
2-hydroxy-4-n-propyl-5-ethyl-1,3,2,-dioxaphosphorinane
B.P. — 110°-114° C/0.02 mm Hg
$n_D^{20}$ — 1.461
The same cyclic phospnites may also be prepared by transesterification of a dialkyl phosphite with a β-glycol (Ostwald, Can. Chem., 37, p.1498).

Compounds of formulae $II_A$ and $II_B$ may be prepared by alkaline hydrolysis of the corresponding compounds I. By this means, sodium O(3-hydroxypropyl) phosphonate has been prepared.

With shaking, 0.07 mole (8.54g) of 2-hydroxy-1,3,2-dioxaphosphorinane is added to 50 cc of water. After complete dissolution, a solution of 0.07 mole (2.8 g) of sodium hydroxide in 50 cc of water is added dropwise. The reaction is allowed to proceed for 15 minutes, with shaking. The water is driven off, and the product obtained dried under vacuum at room temperature.

Yield — 100%

As the products obtained are hygroscopic, it is difficult to give a correct melting-point.

| | Percentage analysis for $C_3H_8O_4PNa$ | | |
|---|---|---|---|
| Analysis | C% | H% | P% |
| Calculated | 22.22 | 4.94 | 19.14 |
| Found | 22.13 | 5.16 | 19.07 |

In the same way, starting from the corresponding 2-hydroxy 1,3,2-dioxphosphorinanes, the following linear compounds have been obtained, each dissymetric cyclic compound giving rise to a mixture of two isomers of formulae $II_A$ and $II_B$, as shown by nuclear magnetic resonance studies carried out on these products.

give the active compounds of formulae I and II on dissolving in water.

The following examples illustrate, without representing limits, the fungicidal properties of the following compounds:

1. 2-hydroxy-1,3,2-dioxaphosphorinane
2. 2-hydroxy-4-dioxaphosphorinane
3. 2-hydroxy-4,6-dimethyl-1,3,2-dioxaphosphorinane
4. 2-hydroxy-4-n-propyl 5-ethyl-1,3,2-dioxaphosphorinane
5. sodium O(3-hydroxypropyl-phosphonate
6. mixture of sodium O(3-hydroxy-3-methylpropyl)-phosphonate and sodium O(3-hydroxy 1-methylpropyl) phosphonate
7. sodium O(3-hydroxy-1,3-dimethylpropyl) phosphonate
8. sodium O(3-hydroxy-2,2-dimethylpropyl) phosphonate
9. mixture of sodium O(3-hydroxy-1-n-propyl-2-ethylpropyl) phosphonate and sodium O(3-ethyl-3-n-propylpropyl) phosphonate.

EXAMPLE 1

Test in vivo with *Plasmopara viticola* (phycomycetes) on vine plants.

a. Preventative treatment

| $II_A + II_B$ | Molecular formula | Physical constants | Yield | Percentage analysis calculated | found |
|---|---|---|---|---|---|
| HO—CH(CH₃)—CH₂—CH₂—O—P(O⁻)(H)(O) Na⁺ | $C_4H_{10}O_4PNa$ | Hygroscopic product | 100% | C 27.27<br>H 5.68<br>P 17.61 | 25.32<br>6.32<br>16.52 |
| HO—CH₂—CH₂—CH(CH₃)—O—P(O⁻)(H)(O) Na⁺ | | | | | |
| HO—CH₂—C(CH₃)₂—CH₂—O—P(O⁻)(H)(O) Na⁺ | $C_5H_{12}O_4PNa$ | M.P. 157–159° C | 100% | C 31.60<br>H 6.32 | 31.84<br>6.34 |
| HO—CH(CH₃)—CH₂—CH(CH₃)—O—P(O⁻)(H)(O) Na⁺ | $C_5H_{12}O_4PNa$ | Hygroscopic product | 100% | C 31.58<br>H 6.32<br>P 16.32 | 31.54<br>6.32<br>16.19 |
| HO—CH₂—CH(C₃H₇)—CH(C₂H₅)—O—P(O⁻)(H)(O) Na⁺ | $C_8H_{18}O_4PNa$ | Hygroscopic product | 100% | C 41.38<br>H 7.76<br>P 13.36 | 41.26<br>7.98<br>13.24 |
| HO—CH(C₃H₇)—CH(C₂H₅)—CH₂O—P(O⁻)(O) Na⁺ | | | | | |

They may also be obtained via known methods of preparation of phosphorous acid monoesters, for example (Journal of Chemical Engineering of the Academy of Chemistry of the USSR, 1972, volume 42, page 1930) by dealkylation of the corresponding diesters with metal halides following the reaction:

It is possible to end up with the same result by treatment of a dialkylphosphite with a base (sodium hydroxide or ammonia) — cf. J. Org. Chem., 1962, p. 2521.

In other respects, the applicant has noticed that, during storage, the compounds covered by the invention tend to self-condense, forming much more viscous oligomers. These products redissociate very readily to Vine plants (Gamay), pot-cultivated, are sprayed on the underside of the leaves with an aqueous suspension of a wettable powder of the following composition by weight:

| | |
|---|---|
| -active material under test | 20% |
| -deflocculant (calcium lignosulphate) | 5% |
| -wetting agent (sodium alkylarylsulphonate) | 1% |
| -support (aluminum silicate) | 74% | at the desired dilution, containing the active material under test at the level under consideration; each test consists of three repetitions.

After 48 hours, contamination is carried out by spraying on the underside of the leaves an aqueous suspension of about 80,000 units/cc of fungal spores. The pots are then placed for 48 hours in an incubation cell at 100% relative humidity and 20° C.

A check is carried out on the plants 9 days after the infestation. Under these conditions, it may be seen that the compounds 2,3,4 and 8, at the level of 0.5 g/l, provide total protection and compounds 1 and 5 a good protection.

It may also be pointed out that none of the products tested has shown the least phytotoxicity.

b. Treatment after contamination

The same procedure is used as in paragraph (a), with the difference that the contamination is carried out first, then the treatment with the active material under test, observation being made 9 days after the contamination.

Under these conditions, it may be observed that, at the level of 1 g/l, compounds 3,5,6,7 and 8 bring to a complete stop the development of mildew on the vine plants.

c. Systemic test on vine mildew by root absorption

Several vine plants (Gamay), each in a pot containing vermiculite and a nutritive solution, are watered with 40 cc of a solution of the material under test at 0.5 g/l. After 2 days, the vine is contaminated with an aqueous suspension containing 100,000 spores/cc of *Plasmopara viticola*. Incubation is subsequently carried out for 48 hours, in conditions of 100% relative humidity and at 20° C. Observations on the degree of infestation take place after about 9 days, comparing with an infested control which has been watered with 40 cc of distilled water.

Under these conditions, with this level of 0.5 g/l, compounds 1 to 3 and 5 to 9, absorbed by the roots, may be seen to provide complete protection of the vine leaves against mildew, thus proving the systemic character of these compounds.

EXAMPLE 2

Test in vivo on melon seedlings with *Colletotrichum lagenarium* (ascomycetes), responsible for melon antrachnosis Melon seedlings (Cantaloup), 8 days old, are treated by spraying with an aqueous suspension of a wettable powder of the same composition as in example 1 and containing 2 g/l of the product under test, on the topside of the cotyledonous leaves. At the end of 48 hours, a second treatment is carried out under the same conditions. A suspension of spores of *Colletotrichum lagenarium* (100,000 spores/ml) is sprayed with a Fisher-type pistol onto the topside of the leaves, and the young plants incubated for 48 hours in a humid environment. Observations are made 8 to 10 days later.

Under these conditions, compounds 3 and 5 may be observed to provide a good protection against the fungus.

EXAMPLE 3

Test in vivo on celery plants with *Septoria apii* (fungi imperfecti), responsible for celery septoriosis.

Celery plants, Plein Blanc de Paris (Full Paris White) golden variety, cultivated in pots and about 3 months old are used for the test, at the 4 to 5 leaf stage.

The fungicide treatment is effected on two occasions 48 hours apart by spraying, using a Fisher-type pistol, on to the underside of the foliage, each time with an aqueous suspension of a wettable powder of the same composition as in example 1, containing 1 g/l of active material.

The contamination is carried out 24 hours later by spraying a suspension of about 700,000 spores/cc on to the underside of the leaves. The pots are then placed in a humid incubation cell for 72 hours. The plants are checked about three weeks after contamination.

In order for the test to be valid, the two control plants must be infested to an extent of at least 75%.

Under these conditions, compounds 3 and 5 exhibit a good protection of the plants against the fungus.

These examples demonstrate the remarkable fungicidal properties of the compounds covered by the invention, characterized by an immediate and systemic action on phycomycetes such as vine mildew, and associated with an absence of phytotoxicity and an efficacity towards fungi belonging to other families such as ascomycetes and fungi imperfecti.

Interesting results have also been obtained for the control of mildew on tabacco and hops. These compounds have in addition shown themselves effective on other types of parasitic fungus such as : *Peronospora tabacci, Pseudoperonospora humili, Phytophthora cactorum, Phytophthora capsici, Bremia lactucae, Phytophthora infestans, Peronospora sp., Phytophthora palmivora, Phytophthora phaseoli, Phytophthora megasperma, Phytophthora dreschsteri* and other *Phytophthora sp.*, on temperate or tropical cultivations such as : tabacco, hops, market-gardening and especially strawberry, pimento, onion, sweet pepper, tomato, kidney-bean, on ornamental plants, and on pineapple, soybean, citrous, cacao, coconut, rubber tree.

These compounds are thus particularly suited for use in preventative or curative treatment of fungal diseases of plants, especially vine mildew.

The compounds covered by the invention may be used to advantage as mixtures with each other or with other known fungicides like the metallic dinitrocarbamates (manebe, zinebe, mancozebe), the basic salts or hydroxides of copper (oxychloride, oxysulphate), the tetrahydrophthalimides (captane, captafol, folpel), methyl N-(1-butylcarbamyl) 2-benzimidazole carbamate (benomyl), the 1,2-di-(3-methoxy or -ethoxy) carbonyl 2-thioureido benzenes (thiophanates), methyl 2-benzimidazole carbamate, etc;;;either to complete the activity spectrum of the compounds covered by the invention, or to increase their persistence.

The applicant has also observed that these compounds may be mixed with other anti-mildew fungicidal phosphorus derivatives, namely the 2-hydroxy-1,3,2-dioxaphospholanes, the β-hydroxyethylphosphites, phosphorous acid and its salts, the phosphonic monoesters and their salts, the phosphonic diesters, the cyclic diphosphorus compounds and the aminophosphites, which respectively come under the French patent applications Nos. 73.01803, 73.37994, corresponding to U.S. Application Ser. No. 432,492 now abandoned, 73.43081, corresponding to U.S. Application Ser. No. 527,380, 73.45627, corresponding to U.S. application Ser. No. 531,387, 74.08995, corresponding to U.S. application Ser. No. 555,293, 74,10988, corresponding to U.S. application Ser. No. 561,220 and 74.13246 corresponding to U.S. application Ser. No. 564,592.

The levels of application can vary within wide limits, according to the virulence of the fungus and the climatic conditions. In general terms, it is convenient to use compositions containing between 0.01 and 5 g/l of active material.

In practical terms, the compounds covered by the invention are rarely used alone. More often than not, they are used in compositions which include, in general, a support and/or a surface-active agent in addition to the active material covered by the invention.

The term "support" in the sense of the present description designates a material, organic or inorganic, natural or synthetic, with which the active material is associated in order to facilitate its application on the plant, seeds, or on the soil, or its transport, or its manipulation. The support may be solid (clays, natural or synthetic silicates, resins, waxes, solid fertilizers...) or liquid (water, alcohols, ketones, petroleum fractions, chlorinated hydrocarbons, liquefied gases).

The surface-active agent may be an emulsifying, dispersive or wetting agent, ionic or non-ionic. For example, polyacrylic acid salts, lignin sulphonic acid salts, condensates of ethylene oxide on fatty alcohols, fatty acids or fatty amines.

The compositions covered by the invention may be prepared in the form of wettable powders, dusting powders; granules, solutions, emulsifiable concentrates, emulsions, concentrates in suspension, and aerosols.

The wettable powders are usually prepared in such a way that they contain from 20 to 95% by weight of active material, and usually contain, in addition to the solid support, from 0 to 5% by weight of wetting agent, from 3 to 10% by weight of a dispersive agent, and, when necessary, from 0 to 10% by weight of stabilizer(s) and/or other additives such as penetrating agents, adhesives, or anti-clumping agents, coloring, etc... As an example, the composition of a wettable powder is given below:

| | |
|---|---|
| -active material | 50% |
| -calcium lignosulphate (deflocculant) | 5% |
| -anionic wetting agent | 1% |
| -anti-clumping agent, silica | 5% |
| -kaolin (support) | 39% |

Aqueous dispersions and emulsions, for example compositions obtained by diluting a wettable powder or an emulsifiable concentrate covered by the invention with water are included in the general framework of the present invention. Those emulsions may be of the water-in-oil or oil-in-water type and may have a thick consistency like that of a "mayonnaise".

The compositions covered by the invention may contain other ingredients, for example protective colloids, adhesives or thickeners, thixotropic agents, stabilizers or sequestering agents, as well as other well-known active materials with pesticidal properties, in particular acaricides or insecticides.

We claim:

1. A process for the protection of plants against fungal diseases which comprise applying to said plants a fungicidally effective amount of at least one dioxaphosphorinane of the formula

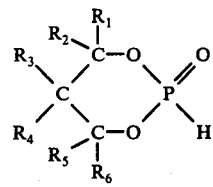

in which each $R_1$, $R_2$, $R_3$, $R_4$, $R_5$ and $R_6$ may be identical or different and represent hydrogen, an alkyl radical, or a halogenated alkyl radical containing from 1 to 5 carbon atoms.

2. A process for protecting plants according to claim 1 wherein $R_1$, $R_2$, $R_3$, $R_4$, $R_5$, $R_6$ represent hydrogen or an alkyl radical containing 1 to 3 carbon atoms.

3. A process for protecting plants according to claim 1 wherein up to 3 of the R groups are alkyl radicals, the rest being hydrogen.

4. A process for protecting plants according to claim 3, wherein the active material is 2-hydroxy-4,6-dimethyl-1,3,2-dioxaphosphorinane.

* * * * *